United States Patent [19]
DeRoos et al.

[11] Patent Number: 5,465,768
[45] Date of Patent: Nov. 14, 1995

[54] FLUID TRANSPORT CONTAINER

[76] Inventors: Bradley G. DeRoos, 41 James St., Sequim, Wash. 98382; John P. Downing, Jr., 260 Kala Heights Dr., Port Townsand, Wash. 98368; Michael P. Neal, 921 Amberly Pl., Columbus, Ohio 43220

[21] Appl. No.: 204,579

[22] Filed: Mar. 1, 1994

[51] Int. Cl.⁶ ........................................ G01N 1/00
[52] U.S. Cl. .................... 141/329; 141/21; 141/114; 141/313; 141/349; 383/66; 73/864.63
[58] Field of Search .................... 141/10, 18, 21, 141/114, 313, 329, 330, 348–350; 383/66, 93, 95, 96; 73/864.63, 864.66

[56] References Cited

U.S. PATENT DOCUMENTS

| | | | |
|---|---|---|---|
| 3,306,563 | 2/1967 | Soto | 141/329 X |
| 3,482,258 | 12/1969 | Steen | 141/329 X |
| 3,917,063 | 11/1975 | Chibret et al. | 141/329 X |
| 3,930,286 | 1/1976 | McGowen | 383/66 X |
| 4,445,550 | 5/1984 | Davis et al. | 141/329 |
| 4,542,530 | 9/1985 | Thomas et al. | 383/66 |
| 4,660,423 | 4/1987 | Armstrong et al. | 73/864.66 X |
| 4,823,623 | 4/1989 | Carpenter et al. | |
| 4,852,413 | 8/1989 | Niskin | 73/864.63 X |
| 5,279,796 | 1/1994 | Parker et al. | |
| 5,350,372 | 9/1994 | Ikeda et al. | 141/329 X |

OTHER PUBLICATIONS

"Appendix B to a Technical Report on the Sampler Used in a Seawater Study Under Naval Research Grant N00014–91–J–4045. 1991", Dr. D. R. Kester, University of Rhode Island.

"1994 Product Catalog, Graseby Nutech, Environmental Products for Source Emission and Ambient Air Monitoring," Graseby Nutech, 4022 Stirrup Creek Drive, Suite 325, Durham, North Carolina 27703–9000.

Primary Examiner—J. Casimer Jacyna
Attorney, Agent, or Firm—Johnnie R. Hynson

[57] ABSTRACT

An improved fluid container for the transport, collection, and dispensing of a sample fluid that maintains the fluid integrity relative to the conditions of the location at which it is taken. More specifically, the invention is a fluid sample transport container that utilizes a fitment for both penetrating and sealing a storage container under controlled conditions. Additionally, the invention allows for the periodic withdrawal of portions of the sample fluid without contamination or intermixing from the environment surrounding the sample container.

4 Claims, 7 Drawing Sheets

FLUID TRANSPORT CONTAINER

This invention is made with Government support under Contract DE-AC06-76RL0 1830, awarded by the U.S. Department of Energy. The Government has certain rights in the invention.

FIELD OF THE INVENTION

The present invention relates generally to a container for the transport, collection, and dispensing of a sample fluid. An advantage of the instant invention is that it maintains the sample fluid integrity relative to the conditions of the location at which it is taken. More specifically, the invention is a fluid sample transport container that utilizes a fitment for both penetrating and sealing a storage container under controlled conditions. This invention allows fluid samples to be taken and maintained under in situ conditions. Additionally, the invention allows for the periodic withdrawal of portions of the sample fluid without contamination or intermixing from the environment surrounding the sample container.

BACKGROUND OF THE INVENTION

Using containers for the collection, transport, and dispensing of fluids is well known in the art. In the pyramids, jars were found that still contained the smell of the perfume from 3000 years ago. The use of a jar and lid arrangement is cost effective and easy to use, but when the jar is opened the contents are exposed to the environment. This arrangement is fine for uses where exposure to the environment is not of concern, such as perfume, beverages, paints, biologic water samples, and other gross sample applications.

Many applications, however, require fluid sample isolation from the environment; other means have been used to maintain sample integrity. For example, the sample can be taken in situ with a container fitted with a lid and sealed on location. This, however, did not solve the problem of exposure to the environment upon retrieval of the sample. An additional problem is that further samples could not be withdrawn without exposing the sample to the environment at the location of analysis.

Another type of sample container that is used to solve this problem utilizes a valve or other flow control mechanisms. The container with the flow control device open is placed in the sample environment and the fluid sample is allowed to flow into the sample container. When full, or when a pre-determined amount of sample is obtained, the valve is then closed. This arrangement solved some of the problems but presented other difficulties. If the container is not full of fluid sample it will affect the distribution of gases; i.e., gas in solution will move into the air space above the sample or vice versa. If the goal of obtaining the fluid sample is to perform a gas-in-solution analysis, the result could be potentially erroneous. An additional problem is pressure equalization. To equalize pressure while using a rigid container, sample fluid or air will have to be added or removed, thereby affecting the sample.

SUMMARY OF THE INVENTION

The instant invention is a sample container for the storage, transport, collection, and dispensing of a fluid that allows the maintenance of sample integrity relative to the sample location. Additionally, the instant invention allows for the periodic withdrawal of portions of the sample fluid without contamination from the container environment at either the point of collection or the location of analysis.

The instant invention can collect, store, transport, and dispense fluids of any type, including but not limited to liquids, chemicals, gases, and slurries. One use that takes advantage of the unique benefits of the instant invention is the collection of water samples from the ocean, lakes, rivers, pools, power plant water systems, or any system where the maintenance of a water sample in an in situ condition is desirable.

Sampling containers can be variable or fixed volume. When used for water sampling, the sample bag can be flexible or rigid. The flexible bag allows for expansion upon filling, and thereby avoids void spaces that could result in air contamination, or in the dissolved gases in the water leaving the solution. These considerations are particularly important when the sample is to be transported from the location where taken, to a remote location for analysis. The instant invention preserves the condition of the sample at the remote location to be substantially the same as it is in situ.

More specifically, the sample container of the instant invention has a sample bag (flexible or rigid) with a fitment assembly sealed to the mouth of the sample bag. The mouth can also be formed when the male fitment is pushed through the female fitment.

The invention has 3 major components; 1) a female fitment, 2) a male fitment, and 3) a sample container or bag. Variable volume containers allow for the most effective use of the instant invention in liquid samples. Fixed volume containers are most effective for gaseous samples. The fluid is introduced into the container by a hose from the location where the sample is drawn.

The male fitment has at least three positions within the female fitment: the first is the stored or unused position; the second is when the male fitment is pushed further into the female fitment such that the septum of the fluid container is punctured; when the male fitment is pushed to the third position no flow is possible in or out of the container.

BRIEF DESCRIPTION OF THE DRAWINGS

FIG. 7a is a bottom view of the insertion tips of the male fitment along lines 7a—7a.

DESCRIPTION OF THE PREFERRED EMBODIMENTS

Figure 1:
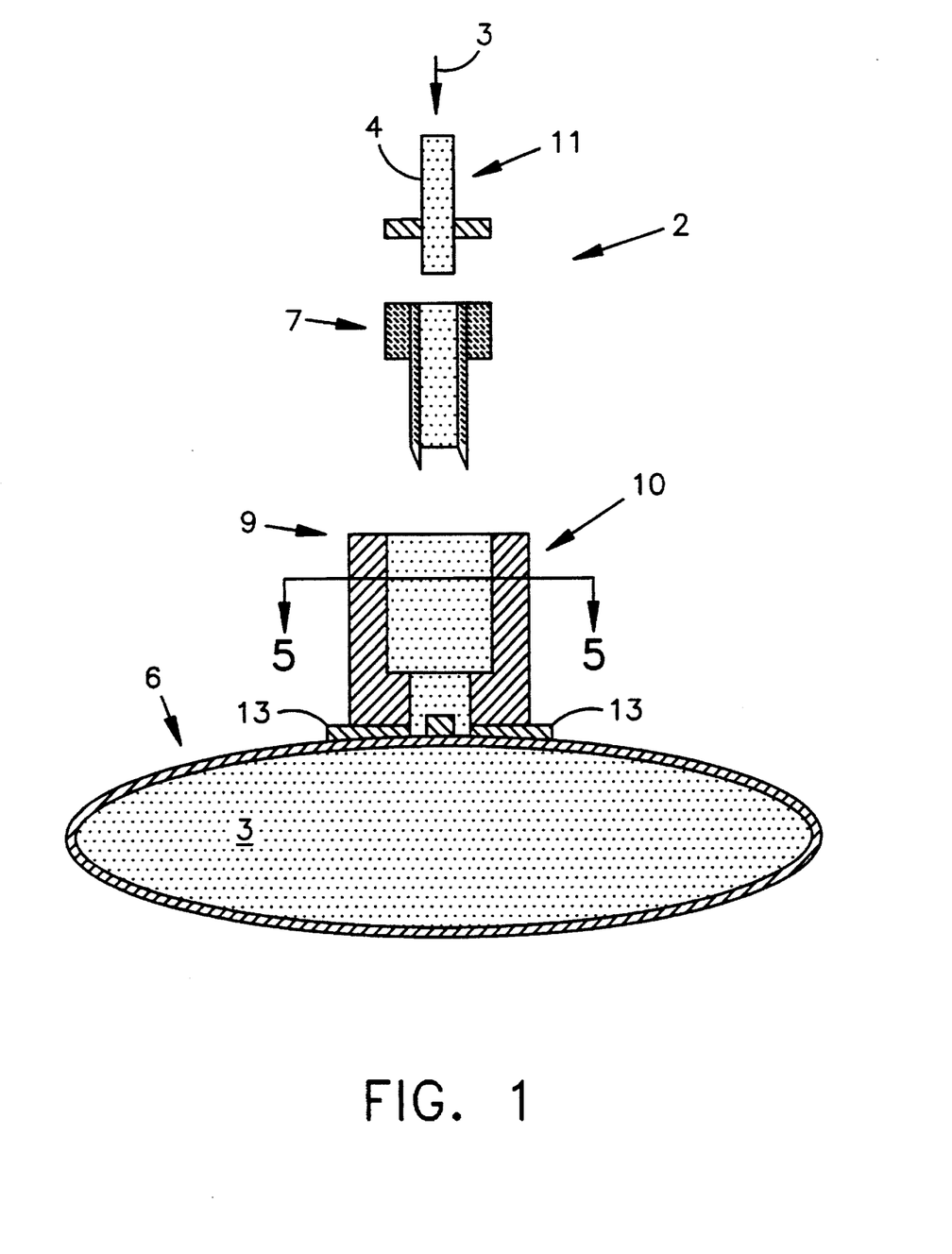
FIG. 1 is a cross-sectional view of the major components of the instant invention.

FIG. 1 is an overall view of the major components of the instant invention which is an fluid container 2 for the sampling, collection, storage, or dispensing of a sample fluid 3. The three major components are a sample bag 6 (or other container), a male fitment 7, and a female fitment 9. Wherein the male and female fitments 7 and 9 make up a fitment assembly 10. Most embodiments will use a fill connection 11; however, sample fluid 3 may enter directly though the fitment assembly 10. The fitment assembly 10, consist of the male 7 and the female 9 fitments, and other attachments that will be discussed with the particular embodiment in which they are used. The fitment assembly 10 is attached to the sample bag 6 with a sealing surface 13. It is obvious to those skilled in the art that the fitment assembly 10 can be attached to the interior or the exterior of the sample bag 6.

One contemplated use of the container 2 is for the collection of fluid samples, such as sea water. The instant invention can collect, store, and dispense a wide range fluids of almost any type. One use that takes advantage of the unique attributes of the instant invention is collection of water samples where it is necessary to maintain the sample in as near an in situ condition is desirable. When used for water collection the sample bag can be flexible or rigid. The flexible bag allows for expansion upon filling, and thereby avoids void spaces that could result in air contamination of the sample, or in the dissolved gases in the water sample leaving solution. Another type of container that solves the problem in a similar manner is a piston within a cylinder arrangement that allows for the space within the chamber to expand or contract as fluid is pumped in or out respectively (not shown). A non-flexible sample bag 6 will appear the same in the empty storage position, or in the filled storage position. The flexible sample bag 6 will appear inflated in the filled storage position when compared to the empty storage position. It will be obvious to those skilled in the art that the container can be constructed in a variety of ways. For example, bellows, metal tank, plastic bag, balloon, or expandable bag configurations.

First Embodiment

Figure 2:
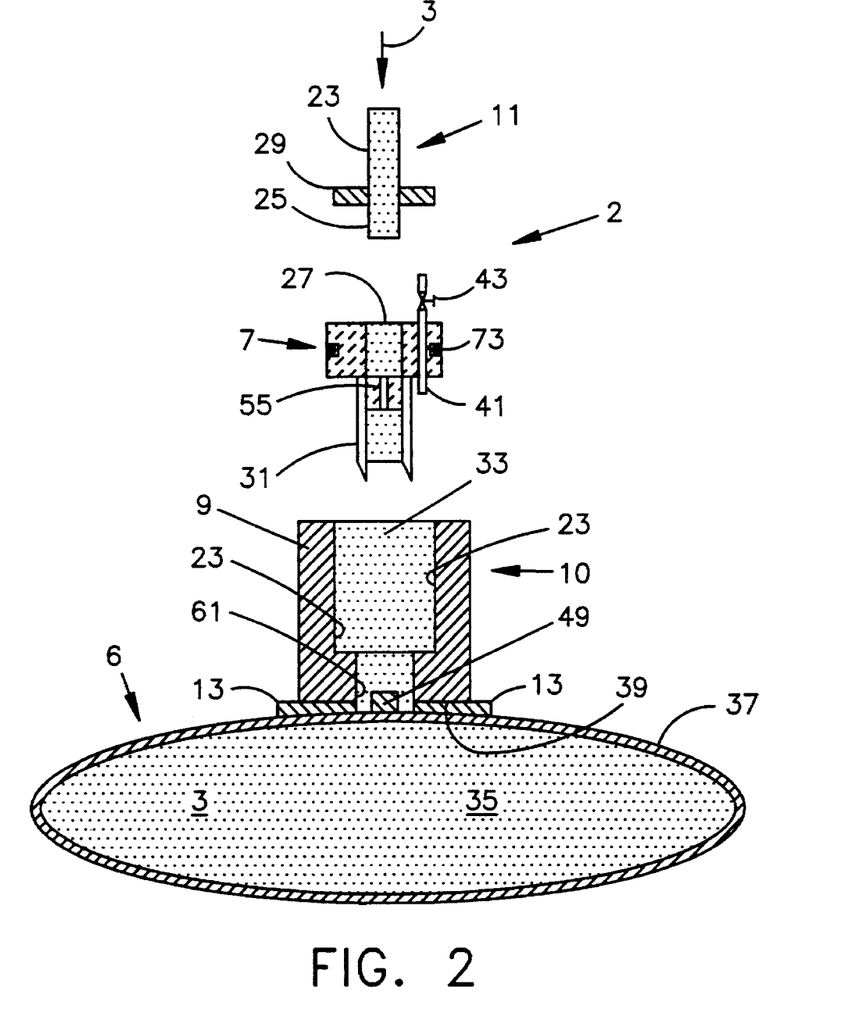
FIG. 2 is a more detailed illustration of the major portions of the instant invention.

FIG. 2 illustrates the more detailed features of a first embodiment. The sample bag 6 is a flexible bag that is illustrated in the distended, or filled condition. If the sample container 2 used is a flexible type, such as triplanar Mylar, it will typically be flat in the storage position (not shown).

Figure 3:
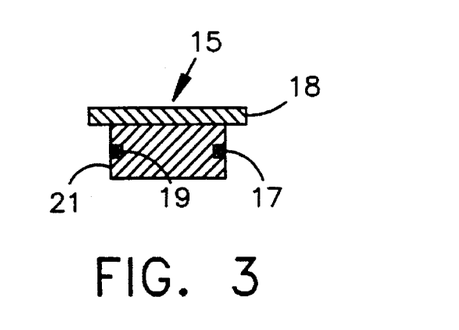
FIG. 3 is cross-sectional view of the dust cap used for sealing the instant invention.

To facilitate the sealing and attachment of the fitment assembly 10 to the sample bag 6, a sealing surface 13 may be utilized that is typically composed of a bonding agent. This sealing surface 13 can be internal or external to the sample bag 6. FIG. 2 also illustrates the typical appearance of a fill connection 11 for filling the fluid container 2. FIG. 3 illustrates a dust cap 15 which can be used to seal the fitment assembly from the environment. The sealing ability of the dust cap 15 can be enhanced by the use of an O-ring 17 in an O-ring grove 19 that is located on the dust cap sealing surface 21. The seal is created by the interface of the dust cap sealing surface 21 and the interior sealing surface 23 of the female fitment.

Bag and Fitment Construction

The typical construction of the sample bags is flexible plastic, rubber, polymer, elastomer, trilaminate film, or mylar. This allows for ease in expansion as the fluid sample flows into the sample bag 6. It should be noted that the selection of the material is, to a large extent, determined by the type of fluid to be sampled. Factors that should be included in the selection of the materials include, but are not limited to: density, toxicity, acidity, the solution base strength (high Ph), and other chemical reactions between the container materials and the fluid to be sampled. The density of the fluid sample is important for two reasons; the first is the permeability of the fluid sample, and the second is the total weight of the sample upon completion. The rigid portions of the male and female fitments are generally constructed of polymers such as PVC or polyethylene, as well as materials such as stainless steel, brass or nickel. Other materials that have sufficient rigidity could also be used.

First Position: Preparation for Sampling

Assembly for use of the first embodiment is illustrated in FIG. 2. The probe end 25 of the fill connection 11 is inserted into the receiving end 27 of the male fitment 7. A fill connection collar 29 is typically provided on the fill connection 11 to facilitate easy handling. The insertion member 31 of the male fitment 7 is then inserted to the first position into the receiving end 33 of the female fitment 9. The first position is defined as where the sample bag septum 35 is intact and the male fitment 7 is positioned within the female fitment 9 with the insertion member 31 above the sample bag septum 35. The sample bag septum 35 is defined as the portion of the exterior surface 37 of the sample bag 6 that is exposed by the attaching end 39 of the female fitment 9.

Flushing and Venting

Figure 4:
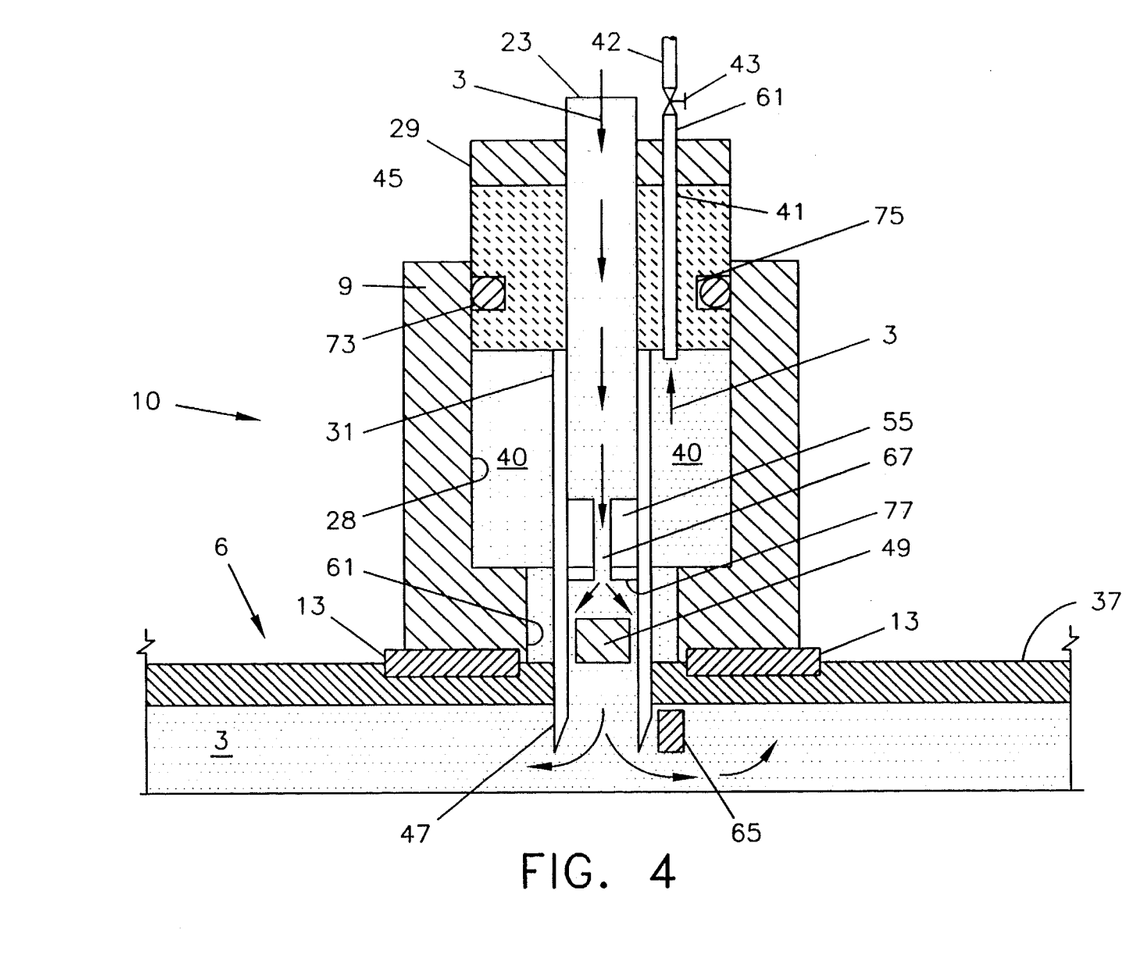
FIG. 4 is an expanded cross-sectional view of the fitment assembly illustrating the fluid sample flow path.

Referring to FIG. 4, the second position is defined as illustrated, and is when the male fitment 7 has penetrated the female fitment 9. The flow path is illustrated in FIG. 4. Specifically, the sample fluid 3 will flow from the fill connection 11 when the flow restriction device, which is typically a hose clamp, is released (not shown). The sample hoses 22 are typically of plastic or rubber construction, and the hose clamps are usually of spring metal construction. While hose clamps are the easiest to use, conventional valves will suffice, while being somewhat less cost effective. For high pressure gases, valves such as gate, globe, or needle valves and rigid piping will serve the purpose.

There are occasions when the collection of samples is required to be under sterile or controlled conditions. The material that is used to construct the sample container 2 can be sterilized or treated prior to use, and will remain in its original condition up to the point of taking fluid into the sample container 2. This will be the case for situations where it is desirable to place within the presealed sample container 2 a substance to treat the fluid sample at the time of filling.

The sample container 2 and the fitment assembly 10 are flushed while filling to remove any impurities or air from air spaces that will form during filling. Referring to FIG. 4, the void 40 within the fitment assembly 10 that is between the male 7 the female 9 fitments, but also applies to any void 40 space that is formed anywhere within the sample container 2. Venting while filling also allows the flushing to take place without contaminants from the environment entering the sample fluid 3 while the sample container 2 is being filled.

Referring again to FIG. 4, to accomplish flushing a vent assembly 41 is added to the male fitment 7 and comprises a vent hose 42 and a flow control device such as a vent valve 43, This will be located ideally close to the upper surface 45 of the male fitment 7.

Prior to inserting the male fitment 7 to the second position, there exists a void 40 in space defined by the area between the male fitment 7 and the female fitment 9. The vent assembly 41 acts as a connection between this void 40 and the environment. When the hose clamp is released and the vent valve 43 is open, sample fluid 3 will flow through the male fitment 7, into the void 40 space and then out to the environment via the vent hose 42. This sample fluid 3 flow flushes the void space of impurities and allows for only sample fluid 3 to be forced into the sample container 2 when the male fitment 7 is moved into the second position. After flushing is completed, the vent valve 43 is shut, which will complete the isolation of the sample fluid 3 from the environment. Depending upon the particular conditions required for the fluid sample, it is possible to continue venting until the sample collection is complete.

The venting assembly 41 can penetrate the male fitment 7 or the female fitment 9. Whichever location is used, consideration should be given to the positioning of the dust cap 15 at the completion of the filling operation. Positioning of the male fitment 7 within the female fitment 9 to avoid interfering with the dust cap 15 insertion is accomplished in several ways. Some embodiments insert the vent assembly 41 into the male fitment 7, while others insert the vent assembly 41 through the female fitment 9. Still other embodiments use a vent assembly 41 that is capable of being withdrawn (not shown).

Second Position: Collecting the Sample

After the fill connection 11 is fitted into the male fitment, and the male fitment is fitted into the female fitment, and the male fitment is pushed to the point that it penetrates the septum 35, the invention will appear as illustrated in FIG. 4, which illustrates the second position. (Note that in the first position the insertion tips 47, at the end of the insertion member 31, is placed in the immediate vicinity of the septum 35, while not penetrating it.) Between the insertion tips 47 is a flow port sealing member 49 that has a flow port sealing surface 51 positioned towards the lower surface 53 of the flow port 55.

Figure 5:
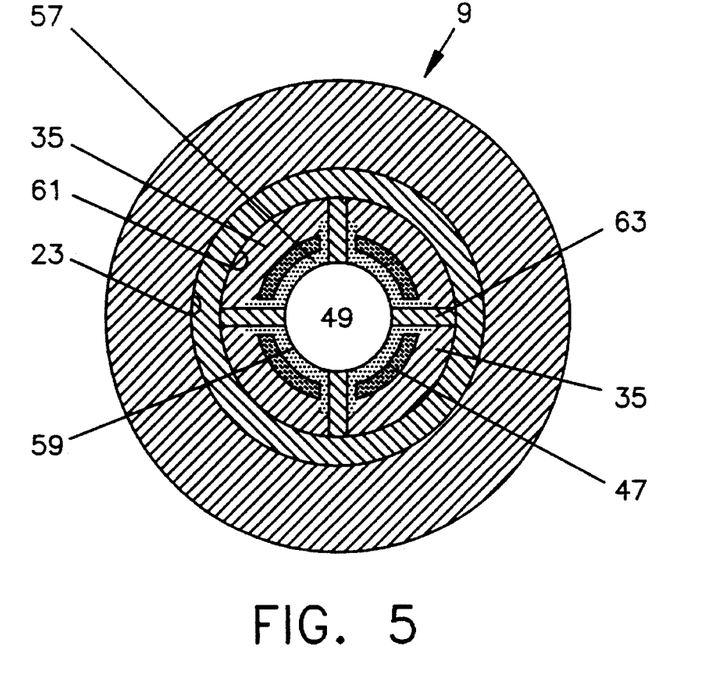
FIG. 5 is a top view of the female fitment along lines 5—5.

FIG. 5 is top view of the female fitment 9 that illustrates the flow aperture 57 that is torn in the septum 35. The maximum extent of the flow aperture 57 is defined by the lateral surface 59 of the flow port sealing member, and the interior surface 61 of the lower portion of the female fitment 9.

Figure 6:
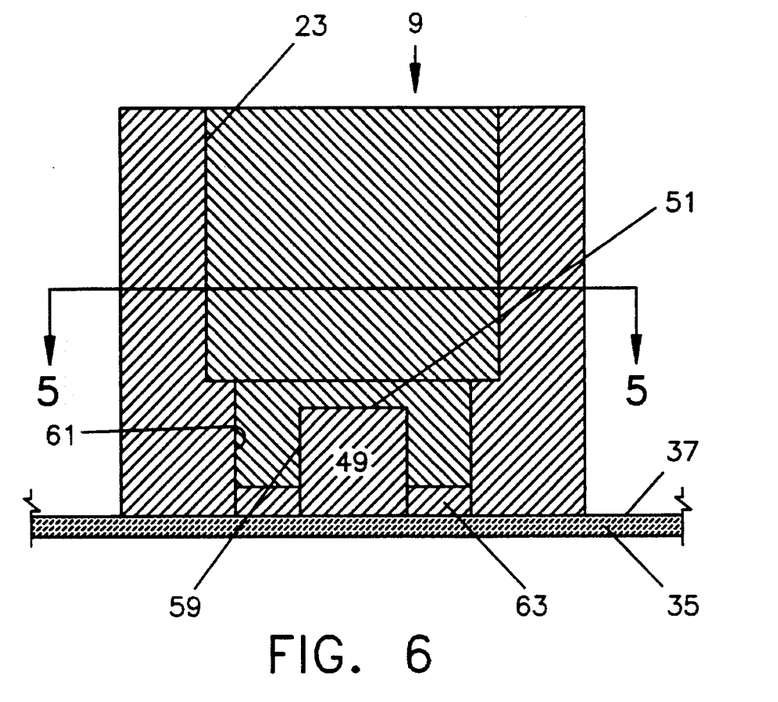
FIG. 6 is a side-cross-sectional view of the female fitment that illustrates the sealing surfaces.

Referring to FIGS. 5 and 6, for ease of construction a cross member 63 will hold the flow port sealing member 49 in position.

Figure 7:
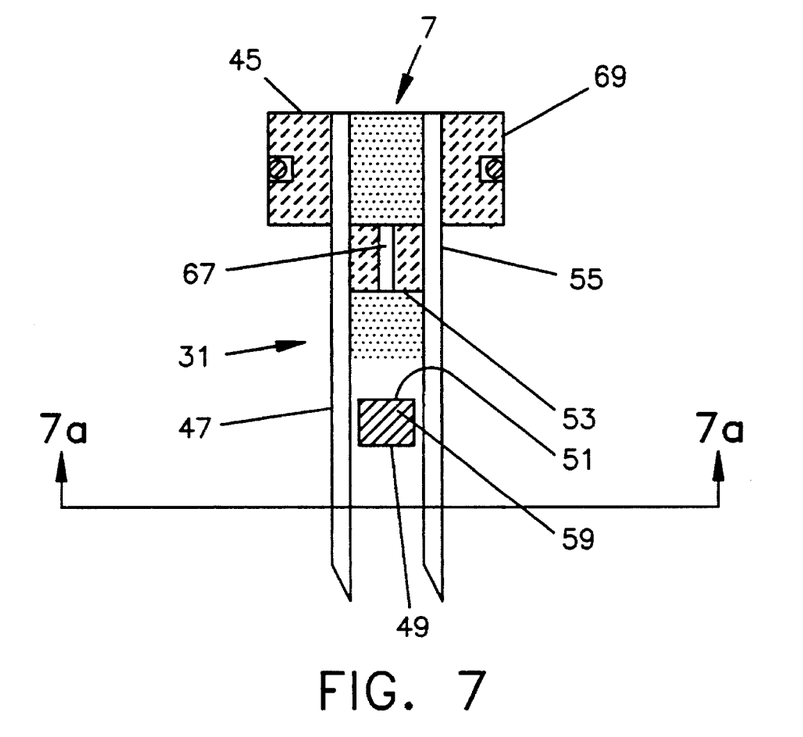
FIG. 7 is an illustration of the sealing surfaces of the male fitment.
Figure 7A:
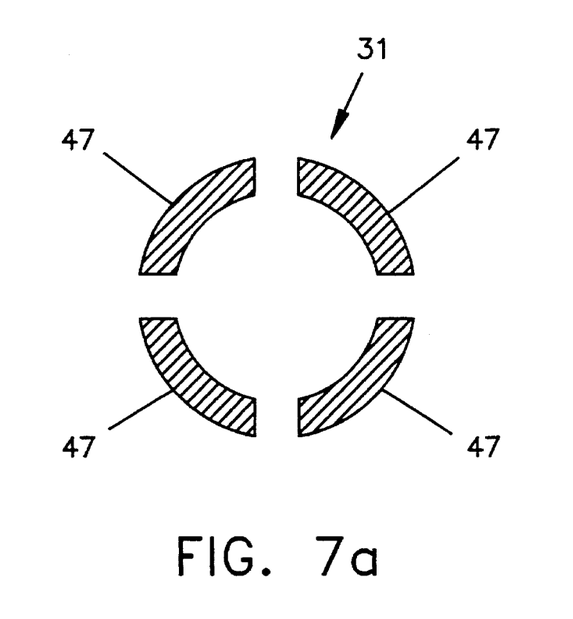

Referring to FIG. 7, which is a side-cross-sectional view of the male fitment 7, it is apparent that male fitment 7 can have a multiplicity of insertion tips 47. FIG. 7a is the bottom view of the male fitment 7 that illustrates the configuration of the insertion tips 47 that fits within the flow aperture 57. FIG. 7 specifically illustrates the instant invention with four insertion tips 47. The insertion member 31 should be separated into insertion tips 47 to facilitate flow, and to allow the relative motion necessary for the sealing surfaces 51 and 53 to come in contact with each other.

Flow Path Description

Referring to FIG. 4, the second position is achieved by pushing the male fitment 7 a portion of the remaining travel distance toward the sample bag. This motion causes the insertion tips 47 to penetrate the septum 35, causing the separated septum 65 to be pushed downward into the interior of the sample bag 6. This penetration creates a flow path that allows the fluid sample 3 into the sample bag 6. The sample fluid 3 enters via the sample hose 4 through the fill connection 11, into the insertion member 31, and from there through the flow control port 67. From there the fluid sample flows down the insertion member 31 toward the flow port sealing member 49. It should be noted that other embodiments have vent groves or ports (not shown) in the insertion member 31 to further facilitate flow, and also an alternative flow path.

The Third Position: Sealing

Referring to FIG. 4, the third position is achieved by pushing the male fitment 7 all of the remaining travel distance toward the sample bag 6. This motion causes the lower surface 53 of the flow port 55 to come in contact with the flow port sealing surface 51. This contact seals off fluid flow into the fluid container 2 that is flowing down the aperture through the male fitment 7. The sealing also prevents sample fluid 2 from flowing from the sample container 2 back into the fill coupling 11. The sealing boundary also prevents contamination of the contents of the sample bag from the environment.

Seal Between the Fitments

Depending upon the particular embodiment design, there could be flow between the fitments that will tend to flow to the environment, via the aperture, that is defined by the horizontal male fitment sealing surface 69 and the horizontal female fitment sealing surface 71. Several means to prevent this flow are available. These include placing an O-Ring 73 in an O-Ring groove 75 in the vertical sealing surface of the male fitment 69.

Another method is to enhance sealing by the use of sealing surfaces of specific design to be impermeable to the type of fluid being sampled or transported. It is well known in the art that different sample fluids require specific types of sealants to prevent escape, or contamination, from the environment into the sample container 2. A coating 77 could be placed on any of the sealing surfaces to enhance sealing.

Use of Dust Cap

Once the fluid sample is isolated and sealed within the sample container 2, an additional measure to ensure boundary integrity should be used. The instant invention utilizes a dust cap 15 for this purpose. To use the dust cap 15, the fill connection 11 is removed. The dust cap 15 is then inserted into the receiving end 33 of the female fitment 9.

The dust cap 15 is also useful is keeping atmospheric contaminants from entering a stored sample container 2.

Position Indicators and Aids

In utilizing the first embodiment it will be helpful to have a readily ascertainable means of determining what position the male fitment 7 is in relative to the female fitment 9. There are several means that are readily apparent to achieve this result. The most practical to date has been to use mutually compatible threads on the vertical male fitmerit sealing surface 69 and the vertical female sealing surface 23. The threads allow easy control of the relative position of the fitments by rotation of the male for female fitment (7 or 9).

Additionally, the threads may be marked to make the relative position quantifiable to an observer. It is apparent to those skilled in the art that a variety of means are available to control the relationship of the fitments. For example, snap-in-place ridges, couplings, positioning members, etc. may be used, but are not critical to the invention.

Removing Fluid Samples

An advantage of the instant invention is that fluid samples 3 can be withdrawn from the sample bag 6 without violating system boundary integrity. The sample containers found in the art require the sample to be exposed to the environment that surrounds the sample container 2 when it is drawn. An additional advantage is that any number of samples can be drawn while maintaining the sample fluid 3 in substantially the same condition as drawn. As mentioned earlier particular materials can be selected to the needs of the specified sample fluid 3 to be handled.

To remove a sample fluid 3 the dust cap 15 is removed and the fill connection 11 is reinserted. The male fitment 7 is then pulled to the second position. Flow of the sample fluid 3 will then occur from the sample bag 6 through the fitment assembly 10 and into the fill connection 11. The fill connection 11 is typically used to convey the sample fluid to the point of analysis.

A SECOND PREFERRED EMBODIMENT

Figure 8:
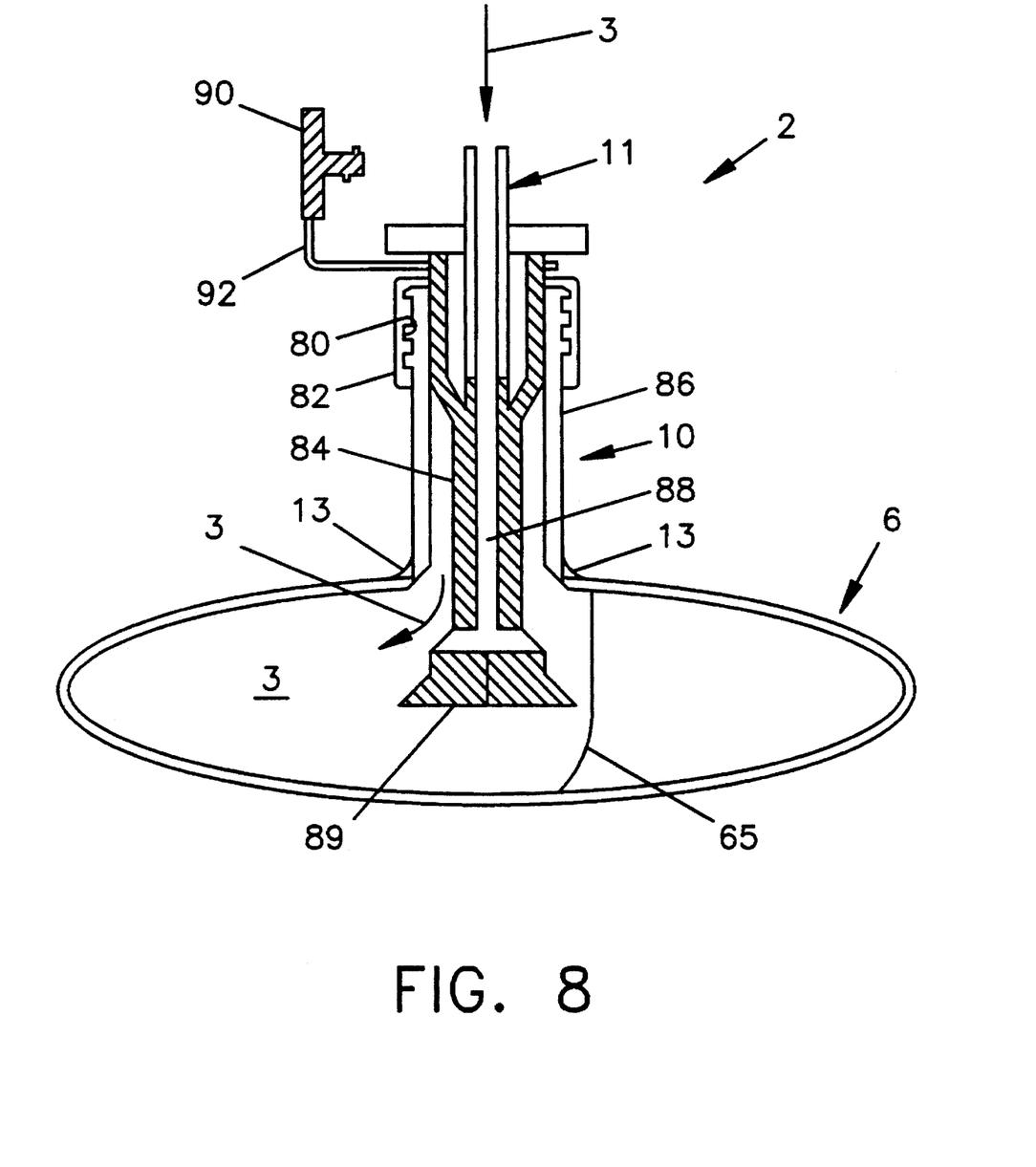
FIG. 8 is a cross-sectional view of the water sample embodiment of the instant invention.

FIG. 8 illustrates a side view of a second embodiment as it will appear if it is full of a fluid sample with the dust cap 90 tethered to the fitment assembly 10. This embodiment of the instant invention that is specifically designed for the taking of water samples. The storage container 2 is shown in the partially filled position.

Figure 8A:
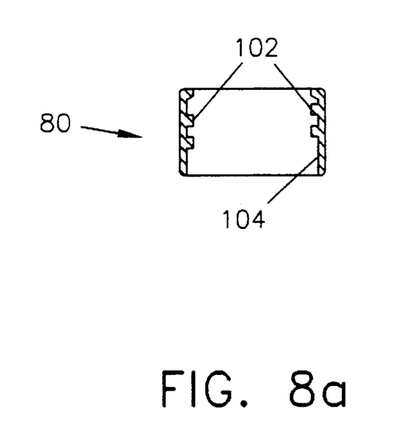
FIG. 8a is a cross-sectional view of the closure nut for the water sample embodiment.
Figure 8B:
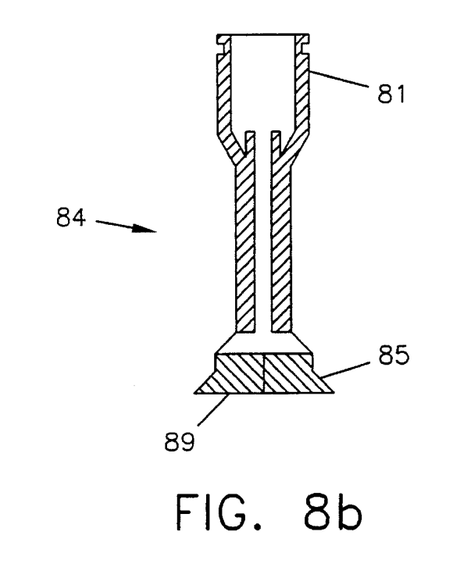
FIG. 8b is a cross-sectional illustration of the sealing surfaces of the male fitment.
Figure 8C:
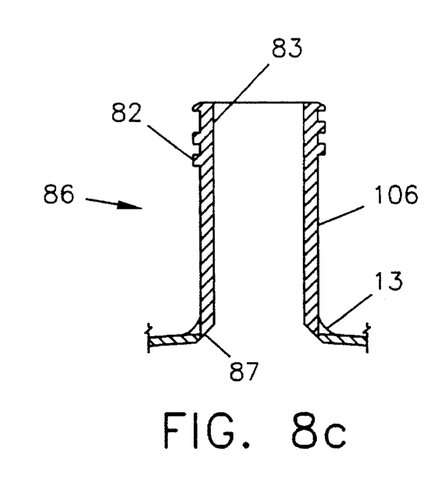
FIG. 8c is a cross-sectional illustration of the sealing surfaces of the male fitment.

This embodiment utilizes a closure nut 80 that has mutually engaging threads 102 to control the movement of the male fitment 84 with respect to the female fitment 86. FIGS. 8a, 8b, and 8c more clearly illustrate the individual components. Specifically, FIG. 8c illustrates the female fitment 86, while FIG. 8b illustrates the male fitment 84. FIG. 8a illustrates the closure nut 80 that controls the movement of the male fitment 84 relative to the female fitment 86.

Flow Path

The closure nut 80 has thread on its interior surface 104, and the female fitment 86 has thread 82 on its exterior surface 106.

Referring to FIG. 8, the fluid sample 3 will enter via the fill connection 11, and then flow though the male fitment flow channel 88 to the sample bag 6. The septum (not shown) will be penetrated by the insertion tip 89 of the male fitment 84, and will create a separated septum 65.

Sealing Surfaces

Referring to FIGS. 8b and 8c, the sealing surfaces in this embodiment will function as discussed above; however, they are disposed of in a different manner. The male fitment sealing surface 85 creates a seal when placed in direct opposing contact with the female fitment sealing surface 87. The upper male fitment sealing surface 81 also seals when placed opposingly from an upper female fitment sealing surface 83.

Dust Cap

Figure 9:
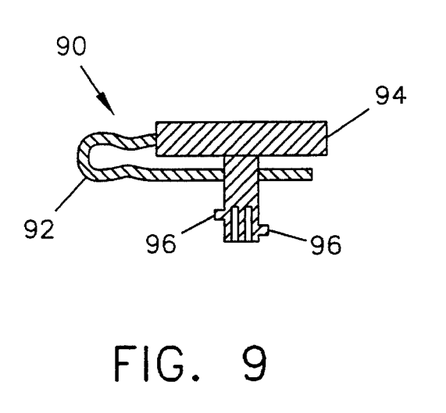
FIG. 9 is a cross-sectional illustration of the dust cap for the water sample embodiment.

Referring to FIG. 9, the dust cap 90 for this particular embodiment has a connecting strap or tether 92 to hold the dust cap lid 94 in place when it is not inserted in the sealed position. While not required, a latching portion (not shown) or dust cap threads 96 may be used to secure the dust cap 15 in its sealing position.

OTHER EMBODIMENTS

While several preferred embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A sample fluid container for the collection, storage, transport, and distribution of a fluid sample, comprising:
   (a) a sample bag;
   (b) a fitment assembly having a male fitment slidably disposed within a female fitment;
   (c) said female fitment being sealably attached to said sample bag;
   (d) said male fitment having a flow port, and further having an insertion member with an insertion tip, said insertion tip having a tip sealing surface disposed toward a female fitment sealing surface;
   (e) a closure nut having threads on a closure nut interior surface that are mutually compatible with threads on an exterior surface of the female fitment, said threads being mutually engaged;
   (f) said male fitment slidably attached to said closure nut;
   (g) wherein transverse circular motion of the closure nut causes vertical motion of the male fitment with respect to the female fitment;
      (i) motion in first direction of said closure nut causing the insertion tip of the male fitment to move toward and puncture the fluid sample bag for fluid sample collection, said fluid sample flowing into said sample bag;
      (ii) motion in a second direction of said closure nut causing the insertion tip of said male fitment to move toward said female fitment sealing surface,
   thereby sealing said sample fluid container.

2. The sample fluid container of claim 1, further comprising a fill connection.

3. The sample fluid container of claim 2, wherein the fill connection is a hose.

4. The sample fluid container of claim 1, wherein the container is sealed from the environment with a dust cap.

\* \* \* \* \*